United States Patent
McKinley et al.

(10) Patent No.: US 9,539,555 B2
(45) Date of Patent: Jan. 10, 2017

(54) APPARATUS AND METHOD FOR HETEROGENEOUS CATALYTIC REACTIONS

(75) Inventors: Donald Hugh McKinley, London (GB); John Richard Hensman, London (GB); John Wilson Kippax, Thornaby (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 14/110,331

(22) PCT Filed: Aug. 24, 2012

(86) PCT No.: PCT/GB2012/052098
§ 371 (c)(1),
(2), (4) Date: Dec. 3, 2015

(87) PCT Pub. No.: WO2013/041836
PCT Pub. Date: Mar. 28, 2013

(65) Prior Publication Data
US 2016/0074824 A1 Mar. 17, 2016

(30) Foreign Application Priority Data
Sep. 22, 2011 (GB) .................................. 1116382.1

(51) Int. Cl.
*B01J 8/00* (2006.01)
*B01J 8/18* (2006.01)
(Continued)

(52) U.S. Cl.
CPC .............. *B01J 8/0492* (2013.01); *B01J 8/003* (2013.01); *B01J 8/0035* (2013.01); *B01J 8/22* (2013.01);
(Continued)

(58) Field of Classification Search
CPC ............. B01J 8/00; B01J 8/0015; B01J 8/003; B01J 8/0035; B01J 8/02; B01J 8/04; B01J 8/0492; B01J 8/20; B01J 8/22; B01J 8/224; B01J 8/228; B01J 2208/00743; B01J 2208/00752; B01J 2208/00761; B01J 2208/00796; B01J 2208/00893; B01J 2208/02; B01J 8/18; C07C 67/08; C07C 67/48–67/54; C07C 67/00; Y02P 20/00–20/121; Y02P 20/127
See application file for complete search history.

(56) References Cited

U.S. PATENT DOCUMENTS 3,091,586 A * 5/1963 MacLaren ............... C10G 45/02
196/46
5,062,270 A * 11/1991 Haut ....................... F25J 3/0209
62/629

(Continued)

OTHER PUBLICATIONS

International Search Report and Written Opinion for PCT/GB2012/052098, dated Nov. 23, 2012, 10 pages.

*Primary Examiner* — Natasha Young
(74) *Attorney, Agent, or Firm* — Armstrong Teasdale LLP

(57) ABSTRACT

An apparatus for use in heterogeneous catalytic reactions comprising a column reactor comprising a plurality of trays mounted one above another, each adapted to hold a predetermined liquid volume and a charge of particles of a solid catalyst thereon; means for introducing a liquid phase reactant above the uppermost tray; means for introducing a vapor phase reactant below the lowermost tray; means for removing a liquid phase post-reaction stream from below the lowermost tray; means for removing a vapor phase post-reaction stream from above the uppermost tray; vapor upcomer means associated with each tray adapted to allow vapor to enter that tray from below; undertow means asso- (Continued)

Figure 1:
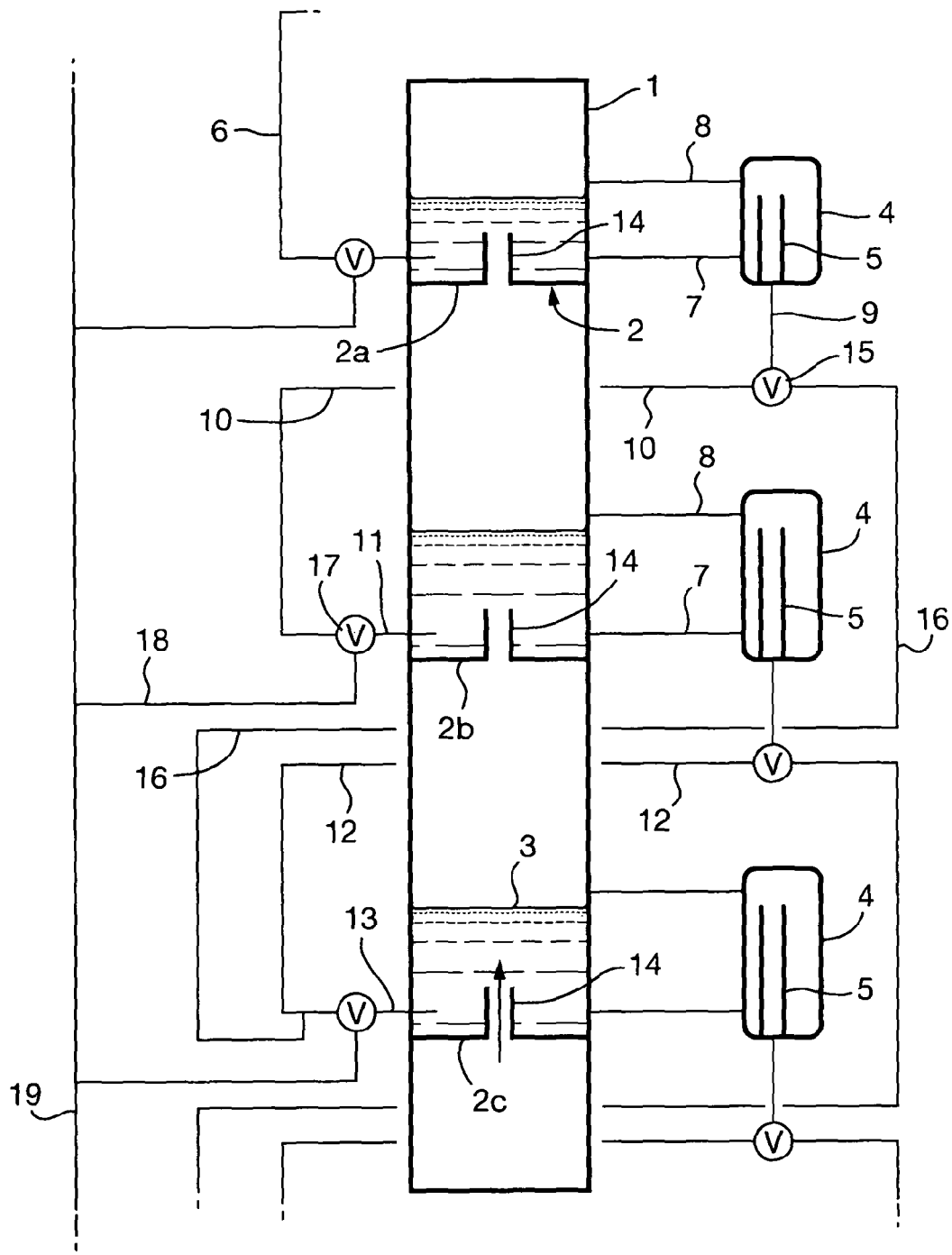

ciated with each tray adapted to remove liquid from that tray and the column reactor before being introduced into the column reactor at a lower tray; means for temporarily directing said liquid removed from a tray to bypass at least one lower tray and be reintroduced to the column reactor at a tray located below said at least one bypassed tray; means for removing the liquid and catalyst from said at least one bypassed tray: and means for replacing a liquid and catalyst inventory on said at least one bypassed tray.

13 Claims, 2 Drawing Sheets

(51) Int. Cl.
*B01J 8/20* (2006.01)
*B01J 8/22* (2006.01)
*C07C 67/00* (2006.01)
*C07C 67/08* (2006.01)
*C07C 67/48* (2006.01)
*C07C 67/52* (2006.01)
*C07C 67/54* (2006.01)
*B01J 8/04* (2006.01)

(52) U.S. Cl.
CPC ............... *B01J 8/228* (2013.01); *C07C 67/08* (2013.01); *C07C 67/54* (2013.01); *B01J 2208/00752* (2013.01); *B01J 2208/00761* (2013.01); *B01J 2208/00893* (2013.01); *B01J 2208/02* (2013.01); *Y02P 20/127* (2015.11)

(56) References Cited

U.S. PATENT DOCUMENTS

| | | | |
|---|---|---|---|
| 5,133,942 A | | 7/1992 | Jones |
| 5,157,168 A | | 10/1992 | Wilmott et al. |
| 5,198,196 A | | 3/1993 | Jones, Jr. |
| 5,252,198 A | * | 10/1993 | Harrison .................... B01J 8/22 208/208 R |
| 5,510,089 A | | 4/1996 | Jones |
| 5,536,856 A | | 7/1996 | Harrison et al. |
| 6,036,848 A | * | 3/2000 | Dessapt ................. B01D 3/009 203/29 |
| 6,241,952 B1 | * | 6/2001 | Ellis ....................... B01J 8/0492 422/220 |

* cited by examiner

APPARATUS AND METHOD FOR HETEROGENEOUS CATALYTIC REACTIONS

This application is a national stage of PCT/GB2012/0152098, now WO 2013/041836, filed Aug. 24, 2012, and claims priority to GB Application No. 1116382.1, filed on Sep. 22, 2011, the disclosures of which are incorporated herein by reference in their entirety.

The present invention relates to apparatus and a method for carrying out heterogeneous catalytic reactions. More particularly it relates to a method and apparatus for carrying out a heterogeneous catalytic reaction for the production of carboxylic acid esters.

Carrying out a reaction in the presence of catalyst in a distillation column such that the reaction is carried out concurrently with the separation of the products of the reaction has been known and practiced for some time. This so-called catalytic distillation is particularly useful for carrying out reversible reactions in the liquid phase such as esterification reactions.

A variety of arrangements have been suggested. Generally the catalyst will be in particulate form. In some arrangements the catalyst is placed on conventional trays within a distillation column. Examples of such catalytic distillation columns include U.S. Pat. No. 5,536,856 and U.S. Pat. No. 5,157,168.

In the arrangement described in U.S. Pat. No. 5,536,856, the contents of which are incorporated herein by reference, esterification is carried out in a column reactor in which there is a plurality of esterification trays. Each tray has a predetermined liquid hold-up and contains a charge of a particulate esterification catalyst. A liquid phase containing the carboxylic acid component flows down the column reactor from one esterification tray to the next tray down against an upflowing alcohol vapour stream which is injected into the bottom of the column reactor. Water of esterification is removed from the top of the column reactor in the vapour stream while ester product is recovered from the sump of the reactor. As the liquid flows down the trays it encounters progressively drier alcohol and the esterification equilibrium reaction is driven further towards ester formation.

As the reaction continues, the catalyst will become deactivated. When this occurs it is necessary to remove the spent catalyst and replace it with fresh catalyst. Conventionally this requires the process to be shut down so that the column can be emptied of catalyst and restocked with fresh catalyst. This is an expensive procedure in terms of the action required and in terms of lost production.

A further problem is that the catalyst in the column may become deactivated at different rates depending on its location in the column. Thus in the situation where the entire process is shut down and the column emptied of catalyst, at least some of the catalyst in the column may not be deactivated and therefore will be replaced unnecessarily. In order to minimise this loss, the point at which shut-down occurs may be delayed until more catalyst has been consumed. However, whilst this may address the above problem, there will be a balance between keeping the process running to prevent loss of active catalyst while needing to replace spent catalyst to maintain efficient production.

In order to address this problem various proposals have been made to enable catalyst to be removed and replaced without requiring total operation to be stopped.

For example, in U.S. Pat. No. 5,510,089 a reactor is described in which small particulate catalyst is loosely supported on trays in a distillation column. The catalyst is submerged in the liquid on the trays and is held in suspension by the upflowing gas. A draw-off is provided for each tray so that liquid containing the suspended catalyst can be removed to a separator during operation. Once removed, the catalyst is separated from the liquid which is recycled to the tray until all of the catalyst has been removed. Fresh catalyst can then be added to the separator where it is slurried into the liquid being recirculated from the tray. The trays can all be connected to the same separator/slurry mixer. Further arrangements for removing catalyst without column shutdown are described in U.S. Pat. No. 5,198,196, and U.S. Pat. No. 5,133,942.

A modified arrangement is described in U.S. Pat. No. 6,036,848. In this arrangement a monophase fluid is diverted to prevent it from passing through the catalyst. The column can then have the spent catalyst removed and have fresh catalyst added. The circulation of the monophase fluid is then restored. The catalyst can be removed by gravity or, if that is inadequate, additional means may be provided. Liquid containing the reagents is introduced into a downtake in the reaction zone. The downtake is located in the centre of the column and comes out into a distribution device from which the liquid is sent to be distributed inside the catalytic bed so as to pass through the catalytic bed upwards from bottom to top. The liquid fraction then pours out of the top of the bed toward the distillation zone located below the reaction zone via an overflow. The distillation zone has an upper distillation plate which comprises an overflow edge which is used to allow the further separation of the liquid fraction containing product. The remaining liquid is then sent towards the next reaction zone positioned below the distillation zone where the procedure is repeated.

Whilst these arrangements address the problem of the previous arrangements in which complete shutdown of the column was required, they still suffer from various disadvantages and drawbacks. In particular as the liquid from a tray is diverted to the apparatus in which the catalyst is separated from the liquid, the flow into and out of the column is effected as is the liquid inventory in the column.

It is therefore desirable to provide an apparatus and a method which enable the above-mentioned problems to be overcome. This is achieved by a system in which the tray that has to have the catalyst replaced is by-passed while the catalyst is replaced so that reaction in the remainder in the column can continue.

Thus according to a first aspect of the present invention there is provided an apparatus for use in heterogeneous catalytic reactions comprising:

(a) a column reactor comprising a plurality of trays mounted one above another, each adapted to hold a predetermined liquid volume and a charge of particles of a solid catalyst thereon;
(b) means for introducing a liquid phase reactant above the uppermost tray;
(c) means for introducing a vapour phase reactant below the lowermost tray;
(d) means for removing a liquid phase post-reaction stream from below the lowermost tray;
(e) means for removing a vapour phase post-reaction stream from above the uppermost tray;
(f) vapour upcomer means associated with each tray adapted to allow vapour to enter that tray from below;
(g) underflow means associated with each tray adapted to remove liquid from that tray and the column reactor before being introduced into the column reactor at a lower tray;

(h) means for temporarily directing said liquid removed from a tray to bypass at least one lower tray and be reintroduced to the column reactor at a tray located below said at least one bypassed tray;

(i) means for removing the liquid and catalyst from said at least one bypassed tray; and (j) means for replacing a liquid and catalyst inventory on said at least one bypassed tray.

By this means the liquid and catalyst inventory can be replaced without the overall flow into or out of the column reactor being affected. This is achieved by the use of the underflow and by the fact that the underflow means removes the flow from the column reactor before reintroducing it thereto at a lower tray i.e. that an external system is used. The underflow arrangement ensures that the liquid inventory is substantially constant.

It should be understood that by "external system" we generally mean that the pipework completely leaves the column reactor however, it will be understood that it also covers arrangements where the pipework is within the external shall of the plant construction while still being external of the column reactor which is considered to be the area in which the trays are located.

It should also be understood that by "underflow means" we mean an outlet which is positioned below the liquid-level in a reaction vessel to allow the flow of liquid from below the top surface of said liquid. This is in contrast to an overflow arrangement wherein liquid is removed from the top of the liquid once the liquid level reaches a predetermined level in the reaction vessel.

The underflow means will preferably be configured such that substantially only liquid is removed from said tray via the underflow means. This can be achieved by any suitable means. In one arrangement, a filter may be included at or near the entrance to the underflow means. A cyclone arrangement may also be used.

Liquid removed from a tray via the underflow means may be directed to the tray below, or when one or more trays are being bypassed, a subsequent lower tray, by any suitable means. In one arrangement, the liquid from the underflow means is passed to a vessel including means which allows the liquid level on the tray to be controlled. The means to control the liquid level may be of any suitable configuration and may be a baffle. The baffle will hold liquid in the pot up to the upper level of the baffle. Liquid in excess of the baffle will then overflow the baffle and flow via appropriate pipework to be introduced to the reaction column at a subsequent tray. Means may be included in the pot to enable it to be evacuated if necessary.

The column reactor comprises a plurality of trays. Although two or three trays may suffice, in some cases it will typically be necessary to provide at least about 5 up to about 20 or more trays in the column reactor depending on the reaction to be carried out. Typically each tray will be designed to provide a residence time for liquid on each tray of from about 1 minute up to about 120 minutes, preferably from about 5 minutes to about 60 minutes although again this will depend on the reaction being carried out.

While we have indicated that the means for introducing the liquid and vapour reactants respectively above and below the trays, it will be understood that these will be above the trays on which reaction is being carried out. If, for example, liquid reactant is added below a tray, that tray will not take part in the reaction and as such the addition in this way does not take the apparatus outside the scope of the present invention. A similar situation applies if any vapour is added above a tray. It will also be understood that an analogous situation applies in connection with the removal of the vapour and liquid post-reaction streams.

One or more wash trays may be provided above the esterification trays in order to prevent loss of product, solvent and/or reagents from the column reactor.

The vapour upcomer means associated with each tray may comprise a sparger positioned so that, in operation, it will lie below the surface of the mixture of liquid and solid catalyst on that tray and so that vapour bubbles emerging therefrom will agitate said mixture of liquid and solid particulate catalyst. The sparger may be a ring sparger. At least one baffle means may be mounted in the vicinity of the sparger to enhance the mixing action thereof. For small scale operation a sparger on the axis of the column reactor under a cylindrical baffle can be used.

In one embodiment the sparger is a ring sparger and inner and outer annular baffle means are positioned in the vicinity of the sparger and define an upflow zone in the region of upflowing vapour bubbles and adjacent downflow zones within and outside the upflow zone.

It is important to avoid stagnant zones where solid catalyst can settle out because this can lead to excessive formation of by-products or to occurrence of hot spots. Although mechanical stirrers can be provided on each tray to maintain the catalyst particles suspended in liquid, this adds somewhat to the complexity of the reactor. However, it is possible, by suitable design of the sparger and tray, to ensure that the upflowing vapour provides sufficient agitation in passage through the liquid on the tray to maintain the catalyst particles in suspension. To achieve this end it is convenient if at least a part of the floor of one or more, and preferably all, of the trays slopes towards a zone where there is turbulence caused by the upflowing vapour such as is to be found under the sparger. The angle of slope is preferably selected so as to be equal to or greater than the angle of repose of the solid particulate catalyst under the liquid in the tray. The adoption of such a slope will tend to ensure that all of the catalyst is in dynamic contact with the liquid during operation and that no stagnant zones of catalyst are formed. Such stagnant zones are undesirable because they can enable undesirable side reactions or even thermal runaway to occur in certain instances.

In the arrangement of the present invention, the liquid on the bypassed tray is used to discharge the catalyst from that tray without the need for the circulation of liquid or addition of fresh liquid to remove the catalyst. Thus the liquid inventory is maintained.

Once removed, the catalyst from the bypassed tray is removed from the liquid. This may be achieved by any suitable means. In one arrangement, the catalyst is separated by filtration. The use of filtration rather than settling allows for a relatively quick turnaround time.

Fresh catalyst is then slurried in a volume of liquid required to replace the liquid on the bypassed tray and returned to the bypassed tray which can then be put back on stream. It will be understood that by "fresh" catalyst we mean either new catalyst or regenerated catalyst. Thus the catalyst and liquid inventory can be replaced without the need for the circulation of liquid or the use of additional liquid to replace the catalyst.

The liquid used to slurry the fresh catalyst may be the liquid previously removed from the tray, fresh liquid or a mixture thereof.

The apparatus of the above first aspect may be used for carrying out a variety of heterogeneous catalytic reactions.

Thus according to a second aspect of the present invention there is provided a process for carrying out a heterogeneous catalytic reaction comprising:

(a) supplying a liquid phase reactant to the apparatus of the above first aspect;
(b) supplying a vapour phase reactant to the apparatus of the above first aspect;
(c) passing the liquid phase reactant and vapour phase reactant in countercurrent through the column reactor, said reactor being maintained under reaction catalyst to allow reaction to occur;
(d) as required carrying out a catalyst replacement process comprising:
  i. directing liquid from a tray to bypass at least one tray located below said tray;
  ii. removing liquid and catalyst on the at least one bypassed tray;
  iii. replenishing said at least one bypassed tray with a charge of liquid and catalyst;
  iv. directing liquid from the tray to the previously bypassed at least one tray;
(e) recovering a liquid phase post-reaction stream; and
(f) recovering a vapour phase post-reaction stream.

The process may additionally include separating the removed liquid from the removed catalyst. This may be achieved by any suitable means such as filtration. The removed catalyst may be washed before being discharged. Fresh catalyst may be washed before being used to replenish the bypassed tray.

Generally the system used for the removal and replenishment of catalyst will be purged before operation to remove oxygen. It will generally be purged with an inert gas such as nitrogen.

The heterogeneous catalytic reaction can be any suitable reaction. In one arrangement it is an esterification process. In particular, it is a process for the production of carboxylic acid esters by reaction of a carboxylic acid component selected from mono-, di- and polycarboxylic acids, anhydrides thereof, and mixtures thereof, and of an alcohol component selected from mono-, di- and polyhydric alcohols, phenols, and mixtures thereof, in the presence of a solid esterification catalyst selected from particulate ion exchange resins having sulphonic groups, carboxylic groups or both.

Examples of monoesterification reactions include the production of alkyl esters of aliphatic monocarboxylic acids from alkanols and aliphatic monocarboxylic acids or anhydrides thereof. Such monocarboxylic acids may contain, for example, from about 6 to about 26 carbon atoms and may include mixtures of two or more thereof. Alkyl esters derived from alkanols containing 1 to about 10 carbon atoms may be of particular importance.

Such monocarboxylic acids include fatty acids such as decanoic acid, dodecanoic acid, tetradecanoic acid, hexadecanoic acid, octadecanoic acid, linoleic acid, eicosanoic acid, isostearic acid and the like, as well as mixtures of two or more thereof. Mixtures of fatty acids are produced commercially by hydrolysis of naturally occurring triglycerides of vegetable origin, such as coconut oil, rape seed oil and palm oils, and triglycerides of animal origin, such as lard, tallow and fish oils. If desired, such mixtures of acids can be subjected to distillation to remove lower boiling acids having a lower boiling point than a chosen temperature (e.g. $C_8$ to $C_{10}$ acids) and thus produce a "topped" mixture of acids, or to remove higher boiling acids having a boiling point higher than a second chosen temperature (e.g. $C_{22+}$ acids) and thus produce a "tailed" mixture of acids, or to remove both lower and higher boiling acids and thus produce a "topped and tailed" mixture of acids. Such fatty acid mixtures may also contain ethylenically unsaturated acids such as oleic acid. These fatty acid mixtures can be esterified with methanol to yield methyl fatty acid ester mixtures that can be hydrogenated to yield mixtures of alkanols, e.g. $C_8$ to $C_{20}$ alkanols (often called detergent alcohols), that are acceptable for production of detergents without prior separation of alkanols one from another.

Another class of carboxylic acid esters that can be produced by the process of the invention are dialkyl esters of aliphatic and cycloaliphatic $C_4$ to $C_{18}$ saturated and unsaturated dicarboxylic acids. These can be produced by reaction of alkanols with the dicarboxylic acids or anhydrides thereof, or with mixtures of the dicarboxylic acid and its anhydride. Dialkyl oxalates, dialkyl maleates, dialkyl succinates, dialkyl fumarates, dialkyl glutarates, dialkyl pimelates, and dialkyl azelaates are examples of such dicarboxylic acid esters. Other examples of such esters include dialkyl esters of tetrahydrophthalic acid. The $C_1$ to $C_{10}$ alkyl esters of such dicarboxylic acids are of particular interest. Either the free dicarboxylic acid or its anhydride, if such exists, or a mixture of dicarboxylic acids and anhydride can be used as the carboxylic acid component starting material for production of such dialkyl esters. Alkyl esters of aromatic $C_7$ to $C_{20}$ monocarboxylic acids and mixtures thereof can be made by a process of the invention. Benzoic acid and 1-naphthoic acid are examples of such acids.

Alkyl esters of aromatic $C_8$ to $C_{20}$ dicarboxylic acids can also be produced by the process of the invention from the acids, their anhydrides and mixtures thereof.

It is also possible to produce polyalkyl esters of polycarboxylic acids by the process of the invention. Such polycarboxylic acid moieties include, for example, citric acid, pyromellitic dianhydride, and the like.

Carboxylic acid esters of dihydric and polyhydric alcohols can be produced by the process of the invention. Examples of such esters include ethylene glycol diformate, ethylene glycol diacetate, propylene glycol diformate, propylene glycol diacetate, glyceryl triacetate, hexose acetates, and the acetate, propionate and n-butyrate esters of sorbitol, mannitol and xylitol, and the like.

The more volatile of the carboxylic acid component and the alcohol component will often be the alcohol component. For example methanol will be the more volatile component in the production of methyl fatty acid esters from fatty acid mixtures obtained by the hydrolysis of triglycerides. In contrast, in the production of the di-n-butyryl ester of ethylene glycol from n-butyric acid and ethylene glycol, for example, n-butyric acid will be the more volatile component. Similarly, in the production of propylene glycol diformate from propylene glycol and formic acid, the more volatile component will be the carboxylic acid component, i.e. formic acid.

The esterification conditions used in the column reactor will normally include use of elevated temperatures up to about 160° C. For example a temperature in the range of from about 80° C. to about 140° C., preferably in the range of from about 100° C. to about 125° C. may be used. Such operating temperatures will be determined by such factors as the thermal stability of the esterification catalyst, the kinetics of the esterification reaction and the vapour temperature of the vaporous component fed to the base of the column reactor at the relevant inlet pressure. Typical operating pressures at the vapour inlet of the column reactor range from about 0.1 bar to about 25 bar. A liquid hourly space velocity through the column reactor in the range of from about 0.1 hr$^{-1}$ to about 10 hr$^{-1}$, typically from about 0.2 hr$^{-1}$ to about 2 hr$^{-1}$, may be used.

The liquid phase reactant may be supplied to an upper part of the column reactor in neat form, in solution in recycled product or in solution in an inert solvent or diluent therefor.

Where the reactants are those for esterification, the alcohol component and/or the carboxylic acid component may be pre-reacted prior to introduction to the column reactor. Such pre-reaction may be used, for example, in a case in which reaction between the two components can be initiated in the absence of added catalyst. The reaction of an acid anhydride, such as maleic anhydride or phthalic anhydride, with an alcohol component, such as an alkanol, for example, methanol, ethanol or n-butanol, is an example of such a reaction, the formation of the corresponding monoester occurring under moderate conditions, e.g. 60° C. and 5 bar, without the need of any added catalyst. This monoester is still a monocarboxylic acid. In addition some formation of diester will occur. The resulting reaction mixture may contain a mixture of monoester, diester, water, and alkanol. Further alkanol can be added, if desired, to the mixture prior to introduction to the column reactor for conversion of the monoester to the diester.

In other cases, even when a monocarboxylic acid ester is the desired product, the alcohol component and the carboxylic acid component can be reacted to equilibrium in the presence of an acidic ion exchange resin containing —SO$_3$H and/or —COOH groups prior to introduction of the resulting equilibrium mixture to the column reactor.

In the process of the invention a vaporous mixture exits the column reactor as an overhead product. Provision may be made for scrubbing such vaporous mixture with the more volatile component, usually the alcohol component, in liquid form in order to wash traces of carboxylic acid ester product and of the other component, usually the carboxylic acid component, back into the column reactor. This overhead product from the column reactor can be condensed and treated in known manner to separate its constituents, the recovered water of esterification being rejected and the more volatile component, usually the alcohol, component, being recycled for re-use in as dry a form as is practicable within the relevant economic constraints.

The lower the water content of the vapour that is supplied to the lowermost one of said esterification trays, the further towards 100% conversion to ester the esterification equilibrium reaction can be driven and the lower the residual acidity of the ester containing product recovered from the bottom of the column reactor will be. However, a balance may often have to be struck between the cost of providing, for example, a substantially dry alkanol for vaporisation into the column reactor, on the one hand, and the cost of providing and operating any additional downstream processing facilities that may be required to upgrade the ester product to the required quality if a less dry alkanol is used. This will vary from alkanol to alkanol and will depend upon the interaction between water and alkanol, for example azeotrope formation, and its effect upon alkanol/water separation. Preferably, when using an upflowing alkanol vapour in the column reactor, the water content of the alkanol vapour supplied to the reactor is less than about 5 mole %, and even more preferably is less than about 1 mole %.

The particulate catalyst used will depend on the reaction being conducted. Where the reaction is an esterification reaction, the solid catalyst may be a granular ion exchange resin containing —SO$_3$H and/or —COOH groups. Macroreticular resins of this type are preferred. Examples of suitable resins are those sold under the trade marks "Amberlyst", "Dowex", "Dow" and "Purolite" such as Amberlyst 13, Amberlyst 66, Dow C351 and Purolite C150.

Different catalysts may be used on different trays of the column reactor. Moreover different concentrations of solid catalyst can be used on different trays.

The charge of solid particulate or granular catalyst on each tray is typically sufficient to provide a catalyst:liquid ratio on that tray corresponding to a resin concentration of at least 0.2% w/v, for example a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. However, the amount of catalyst used should not be so much that it becomes difficult to maintain the catalyst in suspension in the liquid on the tray by the agitation produced by the upflowing vapour entering the tray from below. For a typical catalyst a concentration in the range of from about 2% v/v to about 20% v/v, preferably 5% v/v to 10% v/v may be used.

The particle size of the catalyst should be large enough to facilitate retention of the catalyst on each tray by means of a screen or similar device. However, as the larger the catalyst particle size is the more difficult it is to maintain in suspension and the lower the geometrical surface area per gram, it is expedient to use not too large a catalyst particle size. A suitable catalyst particle size is in the range of from about 0.1 mm to about 5 mm.

As indicated above, the present invention may be used in any heterogeneous catalytic reaction. It is particularly suitable for use in any reactive distillation including those in which an ion exchange catalyst is used.

Further examples of reactions which can be carried out using the present invention include, but are not limited to:
   the formation of pyrrolidines such as from succinates or from lactones such as γ-butyrolactone;
   transesterifications such as the formation of aromatic carbonates from dialkyl carbonate and an aromatic monohydroxy compound, the formation of alkanediol and a dialkyl carbonate from alkylene carbonate and an alkanol, the formation of diaryl carbonate esters by reaction of a dialkyl carbonate and the reaction of an aromatic alcohol to form a diaryl carbonate and an alkyl alcohol, such transesterifications being carried out in an extractive/reactive distillation column in the presence of a transesterification catalyst;
   the production of epoxides from aqueous alkali and halohydrin;
   the production of acetates from acetic acid;
   the production of polyamides;
   the production of dioxylane from ethylene glycol and an aqueous formaldehyde solution;
   propylene oligomerization such as that using a tungstated zirconia catalyst;
   the production of cumene from benzene and propylene using a column packed with a solid acid zeolite catalyst;
   the production of diethylenetriamine (DETA), by continuous reaction of ethylenediamine (EDA) in the presence of a heterogeneous catalyst;
   the alkylation of light aromatic hydrocarbons such as benzene with $C_2$-$C_{30}$ olefins using a solid acid alkylation catalyst;
   the production of monochloroacetic acid from chlorine and acetic acid;

the production of dimethylformamide by reacting methyl formate and dimethylamine;

hydrolysis reactions such as the production of esters, primary and secondary amides and halogenalkanes;

etherification reactions such as the production of MTBE and ETBE and olefin metathesis.

Figure 2:
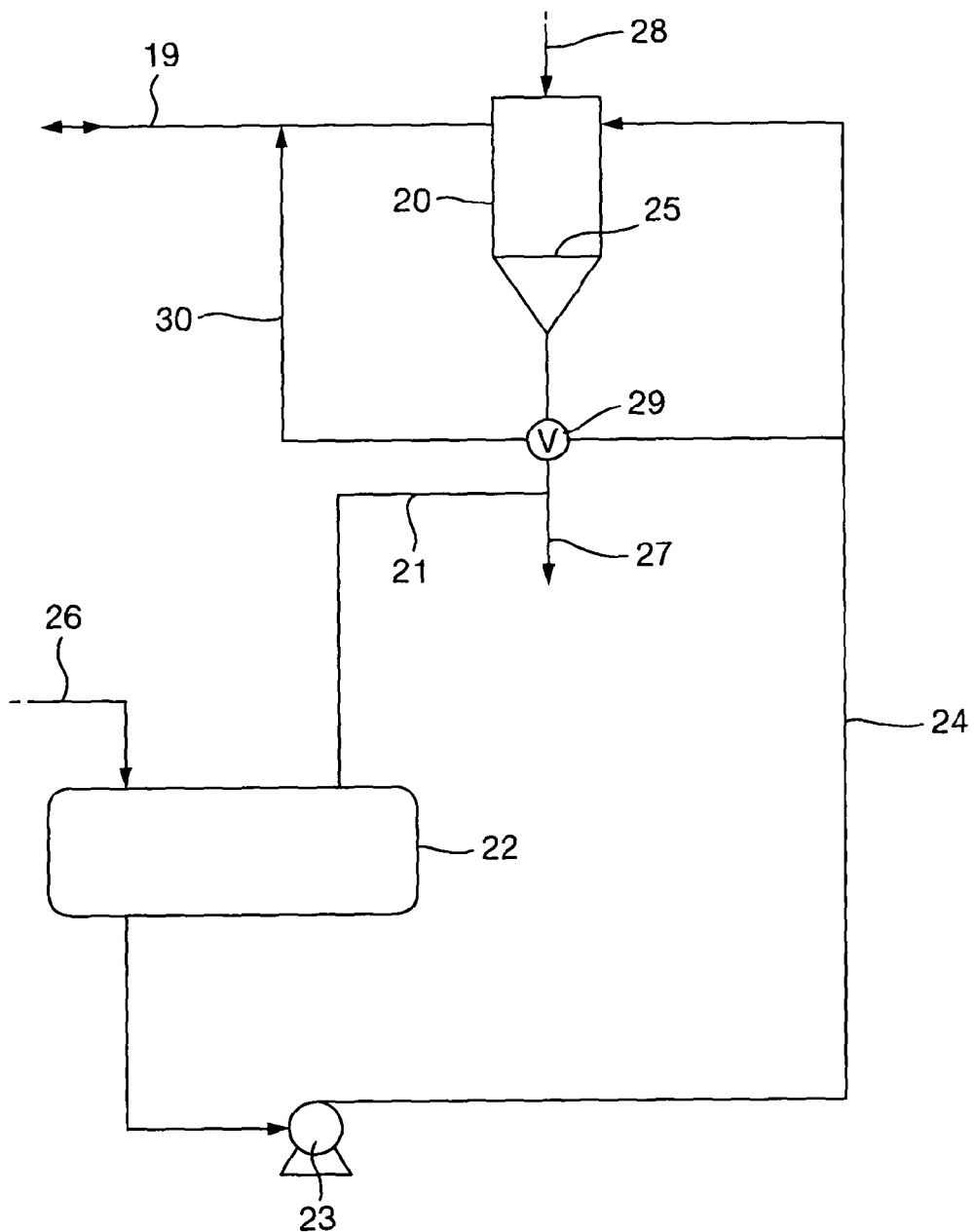

The present invention will now be described, by way of example, with reference to the accompanying drawings in which:

FIG. 1 is a schematic representation of a nozzle and manifold arrangement in a column reactor; and FIG. 2 is a schematic representation of a catalyst handling system for use with the column reactor.

It will be understood that the drawings are diagrammatic and that further items of equipment such as reflux drums, pumps, vacuum pumps, temperature sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

For convenience, the present invention will be specifically described with reference to the esterification of carboxylic acid with an alcohol in the presence of a solid esterification catalyst such as an ion exchange resin containing a —$SO_3H$ and/or —COOH groups. However, the technology is equally applicable to other heterogeneous catalytic reactions which are suitable to be carried out in a catalytic distillation column reactor.

As illustrated in FIG. 1, a distillation column reactor 1 is provided which comprises a plurality of reaction trays 2. These trays can be a horizontal diaphragm or partition that extends within the walls of the reactor 1. This closes off the cross section of the reactor 2 except for the upcomer 4 which is discussed in detail below. For clarity only three trays 2 (2a, 2b and 2c) are illustrated. However, in practice the number of trays will be selected to give the required reaction and separation.

Each tray 2 can retain a volume of liquid, such that there is a liquid level 3. As discussed in more detail below, liquid removed from the tray is passed to a pot 4. The pot 4 comprises a baffle 5 the height of which determines the liquid level on the tray. A vent line 8 may be provided.

In operation, liquid phase reactants introduced into column reactor 1 in line 6 enters tray 2a where it contacts catalyst in a slurry on the tray and vapour flowing up the column such that reaction occurs. Liquid is then removed via underflow 7 and passed to the pot 4. Liquid overflowing baffle 5 leaves the pot 4 in line 9. In normal usage it will then flow in line 10 and be introduced to tray 2b via line 11. The process is then repeated so that liquid leaving tray 2b leaves respective pot 4 and is passed in line 12 and 13 to tray 2c and so on.

Each tray 2 includes means to allow vapour to travel up the column through the liquid held on the trays. In the illustrated arrangement, a vapour upcomer 14 is used.

For ease of reference lines illustrating the addition of the vapour phase and the removal of post-reaction streams have been omitted from the figure.

When an operator wishes to empty a tray, for example tray 2b, the flow of liquid down the column reactor 1 is altered so that the liquid from tray 2a flows directly to tray 2c bypassing tray 2b. In the illustrated arrangement, liquid leaving pot 4 associated with tray 2a rather than being passed in line 10 to tray 2b is directed via valve 15 into line 16 and hence into line 13 for addition to tray 2c.

The used catalyst must then be removed from tray 2b. Valve 17 is then opened to allow the liquid and spent catalyst from tray 2b to be removed in line 18 and then transferred in line 19 to the catalyst handling which is illustrated in FIG. 2.

The tray contents enter the resin loading filter 20 which includes a screen 25. The size of the pores in the screen will be selected to hold the catalyst particles. The liquid component of the tray contents overflow out of the filter 20 and pass in line 21 and pass to the resin loading drum 22. When the liquid has drained out of the filter 21 a valve, not shown, is closed to isolate the filter. The liquid is then pumped using pump 23 via line 24 and 19 back to tray 2b.

When all of the liquid has been transferred to tray 2b, the pump 23 is stopped and the transfer valve 17 is closed. The column tray 2b may be put back on stream by resetting valve 15 to the normal position.

Before the spent catalyst can be discharged to drums it may be necessary to remove any organics from it and return it to the process. This may be achieved by washing the catalyst. Organics such as esters and acids can be removed by washing with alcohol such as methanol. The methanol can then be removed by washing with water. Washing can be achieved by loading the resin loading drum 22 with the washing liquid through line 26. The wash liquid can then be circulated via line 24 to the filter 20. When the catalyst has been washed, the filer can be drained down to the resin loading drum 22 which can then, be emptied of washings. The pump 23 will generally be stopped before the resin loading drum 22 is empty.

The spent catalyst will then be removed from the filter 20 via outlet 27.

It is then necessary to reload the tray with fresh catalyst. Fresh catalyst is loaded into the filter 20 in line 28. The system will then generally be pressure purged with a gas such as nitrogen to remove the oxygen. The resin loading drum 22 is then filled with wash such as methanol. The pump 23 is then operated to transfer the wash liquid to the filter 20 to wash the catalyst. Once the resin loading drum is empty of wash liquid the pump can be stopped.

The liquid inventory from reaction tray 2b on which the catalyst is to be loaded is transferred to the resin loading drum 22 as described above using the bypass system for tray 2b. The liquid form tray 2b is transferred to the resin loading filter 20 and will overflow into the resin loading drum 22. The pump is then operated to allow forward flow to the reaction, tray. The valve 29 will then be opened to allow the flow of catalyst from the resin loading filter 20 into line 30 and hence line 19.

When all the fluid and fresh catalyst has been transferred back to the reaction tray 2b, the pump is stopped and valve 17 is closed to the normal position and valve 15 is altered to put tray 2b back on line.

The invention claimed is:

1. An apparatus for use in heterogeneous catalytic reactions comprising:
(a) a column reactor comprising a plurality of trays mounted one above another, each adapted to hold a predetermined liquid volume and a charge of particles of a solid catalyst thereon;
(b) a first inlet for introducing a liquid phase reactant above the uppermost tray;
(c) a second inlet for introducing a vapour phase reactant below the lowermost tray;

(d) a first outlet for removing a liquid phase post-reaction stream from below the lowermost tray;
(e) a second outlet for removing a vapour phase post-reaction stream from above the uppermost tray;
(f) vapour upcomer means associated with each tray adapted to allow vapour to enter that tray from below;
(g) underflow means comprising an outlet positioned below the liquid level of each tray to allow the flow of liquid from below the top surface of said liquid, the underflow means being associated with each tray and adapted to remove liquid from that tray and the column reactor before being introduced into the column reactor at a lower tray;
(h) a bypass for temporarily directing said liquid removed from a tray to bypass at least one lower tray and be reintroduced to the column reactor at a tray located below said at least one bypassed tray;
(i) a third outlet for removing the liquid and catalyst from said at least one bypassed tray; and
(j) means for replacing a liquid and catalyst inventory on said at least one bypassed tray.

2. Apparatus according to claim 1 wherein the underflow means includes a filter.

3. Apparatus according to claim 1 wherein liquid removed via the underflow means is passed to a pot including means which allows the liquid level on the tray to be controlled.

4. Apparatus according to claim 3 wherein the means to control the liquid level is a baffle.

5. Apparatus according to claim 1 wherein the vapour upcomer means comprises a sparger.

6. Apparatus according to claim 1 additionally including a filter in which catalyst from the bypassed tray is removed from the liquid.

7. A process for carrying out a heterogeneous catalytic reaction comprising:
(a) supplying a liquid phase reactant to the apparatus of claim 1;
(b) supplying a vapour phase reactant to the apparatus of claim 1;
(c) passing the liquid phase reactant and vapour phase reactant in countercurrent through the column reactor, said reactor being maintained under reaction catalyst to allow reaction to occur;
(d) as required carrying out a catalyst replacement process comprising:
 (i) directing liquid from a tray to bypass at least one tray located below said tray;
 (ii) removing liquid and catalyst on the at least one bypassed tray;
 (iii) replenishing said at least one bypassed tray with a charge of liquid and catalyst;
 (iv) directing liquid from the tray to the previously bypassed at least one tray;
(e) recovering a liquid phase post-reaction stream; and
(f) recovering a vapour phase post-reaction stream.

8. A process according to claim 7 further comprising separating the removed liquid from the removed catalyst.

9. A process according to claim 7 wherein the heterogeneous catalytic process is a reactive distillation.

10. A process according to claim 9 wherein the reactive distillation is carried out in the presence of an ion exchange catalyst.

11. A process according to claim 7 wherein the heterogeneous catalytic process is an esterification process.

12. A process according to claim 11 wherein the esterification process is a process for the production of carboxylic acid esters by reaction of a carboxylic acid component selected from mono-, di- and polycarboxylic acids, anhydrides thereof, and mixtures thereof, and of an alcohol component selected from mono-, di- and polyhydric alcohols, phenols, and mixtures thereof, in the presence of a solid esterification catalyst selected from particulate ion exchange resins having sulphonic groups, carboxylic groups or both.

13. A process according to claim 7 wherein different catalysts are used on different trays of the column reactor.

* * * * *